United States Patent [19]

Jaworek et al.

[11] 4,081,329

[45] Mar. 28, 1978

[54] PREPARATION OF CARRIER-BOUND MACROMOLECULAR COMPOUNDS

[75] Inventors: Dieter Jaworek, Weilheim; Karl-Heinz Botsch, Bernried; Günter Weimann; Michael Nelböck-Hochstetter, both of Tutzing; Helmut Determann, Starnberg, all of Germany

[73] Assignee: Boehringer Mannheim GmbH, Mannheim, Germany

[21] Appl. No.: 655,363

[22] Filed: Feb. 5, 1976

Related U.S. Application Data

[63] Continuation of Ser. No. 419,845, Nov. 28, 1973, abandoned.

[30] Foreign Application Priority Data

Dec. 8, 1972 Germany ............................. 2260184

[51] Int. Cl.$^2$ ............................................. C07G 7/02
[52] U.S. Cl. .................................... 195/63; 195/68; 195/DIG. 11; 260/112 R
[58] Field of Search ............... 195/63, 68, DIG. 11; 260/112 R

[56] References Cited

U.S. PATENT DOCUMENTS

| 3,775,253 | 11/1973 | Jaworek et al. | 195/63 |
| 3,791,927 | 2/1974 | Forgione et al. | 195/63 |
| 3,806,417 | 4/1974 | Beaucamp et al. | 195/63 |
| 3,849,253 | 11/1974 | Harvey et al. | 195/68 |

*Primary Examiner*—David M. Naff
*Attorney, Agent, or Firm*—Burgess, Dinklage & Sprung

[57] ABSTRACT

Carrier-bound macromolecular compounds, especially bioactive macromolecular compounds, are produced by reacting a macromolecular compound A with a coupling compound B containing at least one reactive function capable of coupling with compound A and at least one further reactive function capable of polymerization, adding to the resulting coupled reaction product AB an unswollen molecular sieve material having cross-linking sufficient to exclude penetration by compound A, and polymerizing the polymerizable group of the coupled product AB in the molecular sieve material to form a polymer body in the molecular sieve material and fix compound A on the surface of the molecular sieve material. Compound A can be, e.g., an enzyme, antibody or hormone, and coupling compound B typically contains, as the coupable function, an alkylation or acylation group such as oxirane, ethyleneimine, halide, acid halide, azide or anhydride groups, and, as the polymerizable function, a carbon-carbon or carbon-oxygen double bond.

12 Claims, No Drawings

PREPARATION OF CARRIER-BOUND MACROMOLECULAR COMPOUNDS

This is a continuation of Ser. No. 419,845, filed Nov. 28, 1973, now abandoned.

The present invention is concerned with macromolecular compounds, especially bioactive compounds, and with a process for the preparation of such macromolecular compounds. More particularly, the invention relates to bioactive macromolecular compounds which are fixed on to the surface of insoluble carriers.

Carrier-bound macromolecular compounds are known. They can be present on the surface of a carrier material, on which they are either adsorbed or, usually after activation of the carrier material, are covalently bound. Surface carrier-bound macromolecular compounds of this type, for example enzymes, still suffer from considerable disadvantages. In particular, the surface concentration is too low and in the case of biologically-active materials, only part of the activity is present. Furthermore, in the case of fixing on the carrier surface, the yields are usually too low.

Macromolecular and low molecular weight compounds with biological or pharmaceutical activity in which the compounds are physically or chemically embedded in solid carriers are also known. They suffer from the disadvantage that they are scarcely accessible or inaccessible to reaction components so that, in the latter case, only the substances which are bound on to the surface of the carrier can be chemically active. The reactive surfaces of such "biocatalysts" can, for increasing the specific activity, also not be sufficiently increased by comminution of the polymeric carrier used since small particles are mechanically unstable and thus can no longer be used in many cases.

In the case of surface fixing on to activated carriers or on to carriers with ionogenic groups, not all of the reactive groups of the carrier are accessible to the macromolecular substance to be fixed or bound so that the carrier still contains charged groups and, on the other hand, the bonding density of the macromolecular compound never achieves the magnitude to be expected from the number of sites capable of bonding. Macromolecular compounds bound on to a carrier by adsorption are not of universal utility since they can easily be eluted again.

The present invention substantially overcomes the disadvantages inherent in the known carrier-bound macromolecular compounds and in processes used for the preparation thereof and, in particular, provides a process which provides better yields, less inactivation of the macromolecular compound and higher concentrations of the macromolecular compound on the surface of the carrier than hitherto possible.

Essentially, the present invention comprises first coupling a macromolecular compound with a monomeric or low molecular weight compound and then drawing the monomeric or low molecular weight component of the coupled product into a molecular sieve material and polymerizing same therein, to result in the macromolecular compound, which cannot penetrate into the molecular sieve, thereby being fixed on to the surface of a carrier comprising the molecular sieve and, polymerized thereinto, the coupling compound.

Thus, according to the present invention, there is provided a process for the preparation of a carrier-bound macromolecular compound, wherein a macromolecular compound A is first reacted with a coupling compound B, which contains at least one function capable of coupling with the macromolecular compound A and at least one further function capable of polymerization, whereafter there is added a molecular sieve material in unswollen state, the degree of cross-linking of which excludes the macromolecular compound A, and the polymerizable group of the coupled product AB is polymerized in the molecular sieve material, optionally in the presence of further copolymerizable and/or polymerization-promoting compounds.

Thus, according to the process of the present invention, there are obtained new carrier-bound macromolecular compounds in which the macromolecular compounds are covalently bonded on to the surface of a polymer body which penetrates a molecular sieve material body.

Macromolecular compounds according to the present invention include, for example, proteins, especially biologically-active proteins, such as enzymes, hormones and antibodies, nucleic acids, peptides, porphyrins, haemins, phosphatides, cerebrosides, gangliosides, glycosides and the like. It is important that the macromolecule is so large that it practically cannot penetrate into the interstices of the molecular sieve material used. Therefore, the minimum size of the macromolecules which can be bound according to the present invention depends upon the size of the interstices of the molecular sieve material used. Macromolecules which are especially preferred according to the present invention include biologically-active proteins and especially enzymatically-active proteins.

As compound B which, in the process according to the present invention, is coupled with the macromolecular compound A and which possesses at least one function capable of coupling with the latter and at least one further function capable of polymerization, there can be used a large number of compounds, depending upon the functions available for coupling with the macromolecular compound A, as well as upon the nature of the polymer or copolymer to be produced. If, for example, the macromolecula A contains amino acid residues, i.e., is a protein or a peptide or a compound containing them, then the function capable of coupling can be, for example, an oxirane group, an ethyleneimine group, a halide group, an acid halide group, an acid azide group or an acid anhydride group. Further examples include the groups previously used for the acylation or alkylation of amino groups in peptide and protein chemistry; thus, for example, there can be used aldehydes, hydrazines, oxazolones, mixed chloroformic acid esters, esters of carboxylic acids with secondary phosphoric acid esters, secondary arsenic acid esters, hydroxyacetonitrile, N-hydroxysuccinimide, p-nitrophenol, polyhalophenols, dicyclohexyl carboniimide and phenyl triazine, as well as mixed anhydrides of carboxylic acids with sulfuric acid, Leuch's anhydride, Leuch's thioanhydride, carboxylic acid imidazolides, carboxylic acid tolyl-sulfonyl-N-methylamides and acid amides of a carboxylic acid with phenyl-triazine-N-oxide.

In the case of other macromolecular compounds, there are used, depending upon their functional groups suitable of coupling, the alkylation and acylation agents known and suitable for this purpose. In the case of nucleic acids, there can essentially be used the same coupling groups as in the case of proteins and peptides, acid amides, such as normal carboxylic acid amides, alkylamides, morpholides and the like, being especially preferred.

The polyfunctional compound B can contain one or more groups capable of coupling with the macromolecular compounds A but they preferably only contain one such group.

Apart from the coupling function, the compound B has at least one further functional group which can participate in a polymerization reaction. This group may be one suitable for an addition polymerization but also one suitable for a condensation polymerization. Addition polymerizable groups are, in particular, carbon-carbon double bonds, preferably double bonds which are activated in the usual manner, which can enter into homo- and copolymerization reactions, as well as carbon-oxygen double bonds, for example carbonyl groups and the like. Besides groups which, in the actual meaning of the term, are polymerizable, there can also be used groups which are capable of polyaddition, for example, hydroxyl groups, isocyanate groups and caprolactam groups, as well as groups capable of polycondensation.

The preferred groups are those which are suitable, in the narrower sense, of polymerization and co-polymerization, and a particularly preferred group of such compounds has the formula:

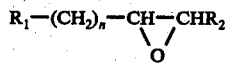

$$R_1-(CH_2)_n-CH-CHR_2$$
$$\diagdown O \diagup$$

wherein $R_1$ is a mono- or polyunsaturated aliphatic hydrocarbon radical, which optionally contains at least one oxo group adjacent to a double bond, and $R_2$ is a hydrogen atom or a lower alkyl radical.

Specific examples of compounds B which can be used according to the present invention include acrylic acid 2,3-epoxypropyl ester, but-2,3-ene oxide, 1-allyloxy-3-(N-ethyleneimino-propan-2-ol), maleic anhydride, allyl bromide, acryloyl chloride, maleic acid azide, methacrylic acid 2,3-epoxypropyl ester, maleic acid 2,3-epoxypropyl monoester, fumaric acid epoxy-(2,3-epoxypropyl diester), 1-(allyloxy)-2,3-epoxybutane and the like. Especially preferred compounds of this type are described, for example in German published specification (DOS) No. 21 28 743.

Molecular sieve materials which can be used according to the present invention are those with a mesh size which excludes the macromolecular compound A but which allows the polyfunctional coupling compound B to pass through. There are preferably used gel-like molecular sieves based on cross-linked polymers, such as polyacrylamide gels and cross-linked carbohydrates, such as cross-linked dextran, agar and the like. Particularly preferred molecular sieve materials are summarized in L. Fischer, "An Introduction to Gel Chromatography", 1969, pp. 182, 188 and 194. Suitable molecular sieve materials can also, to a certain extent, be "made to measure" for the macromolecular compound A and the coupling compound B in question by polymerizing appropriate polymerizable monomers, for example acrylamide, methacrylamide, acrylic and methacrylic acid esters, styrene and the like, with an appropriate amount of a cross-linking compound, for example, N,N'-methylene-bis-acrylamide, tetraethylene glycol dimethacrylate or ethylene diacrylate, divinyl-benzene and the like. The "sieve size" is regulated by the amount of cross-linking agent used, whereby, with an increasing amount of cross-linking agent, the pore size of the sieve decreases. According to the present invention, molecular sieve materials are particularly preferred which are based on cross-linked dextrans and on acryl or methacrylic acid derivatives, especially their amides and esters.

For the process according to the present invention, the molecular sieve material must be wholly or at least partially in unswollen state. This is necessary since the polymerization or copolymerization of the polymerizable function of the coupling compound B is to take place within the molecular sieve. Therefore, the swelling of the molecular sieve is carried out in such a manner that the polymerization system is drawn in through the swollen molecular sieve material and is present substantially in the interior of the molecular sieve material. In the case of the swelling of the molecular sieve, the solution is thereby drawn in which the coupling of the macromolecular compound A with the compound B has taken place so that, in principle, only the macromolecular part of the coupling product AB remains behind on the surface of the molecular sieve body. The volume of the reaction solution is preferably so chosen that it is insufficient for the complete swelling of the molecular sieve, which ensures that the subsequent polymerization takes place exclusively within the molecular sieve body.

By appropriate coordination of the molecular sieve material to the coupling compound B and the other polymerizable system, as well as to the solvent, if one is used, there can be achieved, if desired, a complete filling and penetration of the molecular sieve body with the polymer or a more superficial penetration, with the maintenance of a certain hollow volume within the molecular sieve body.

The polymerizable system can be selected with regard to the polymerization conditions and especially with regard to the polymerization temperature and the polymerization properties of the polymerizable function of the compound B necessary for the maintenance of the properties desired of the macromolecular compound, for example an enzymatic activity. If the macromolecular compound A is a relatively temperature-stable nucleic acid, then a compound B capable of polycondensation at an elevated temperature suffices as the sole component of the polymerization system. If the macromolecular compound A is a temperature-sensitive enzyme, then it is expedient to work under copolymerization conditions with the use of an appropriate comonomer, for example acrylamide, in the presence of a low temperature polymerization catalyst, for example a peroxide, and possibly of an accelerator and/or cross-linking agent. As initiators, there can generally be used the initiators and catalysts which are conventionally employed in polymer chemistry, insofar as they do not affect the activity of the macromolecular compound A. As initiators or catalysts, in the case of olefinically-unsaturated monomers or comonomers, there can be used, for example, inorganic or organic peroxides, azo compounds or the like. In addition, reaction accelerators, such as amines or the like, can also be used. When using acrylic acid or methacrylic acid derivatives as comonomers or as the polymerizable function of compound B, the use of an initiator combination of a peroxydisulfate and an amine, such as dimethylaminopropionitrile, has proved to be especially useful.

In principle, the use of cross-linkable monomers in the polymerization system is not necessary since, due to the polymerization within the molecular sieve meshwork, they always receive the properties of a cross-linked polymer. However, for a modification of the physical properties, it can, nevertheless, be expedient to use a cross-linking agent, i.e. a compound having more than one polymerizable group, such as, for example, those mentioned above.

The invention permits the fixing of even very sensitive macromolecules, in a gentle manner, on to insoluble carriers with maximum activity yields. A special advantage of the present invention is the fact that the fixing takes place in a dissolved system with correspondingly almost quantitative coupling of the macromolecular compound A with the coupling compound B during the coupling or preincubations step. At the same time, however, the present invention makes full use of the advantages of a purely superficial fixing of the macromolecular compound A since this is selectively enriched and fixed on the surface of the polymerization body which coincides with the surface of the molecular sieve body. It is thus possible to ensure a much denser occupation of the polymer body surface with the molecules of the macromolecular compound A than in the case of the previously known fixing methods. Consequently, the carrier-bound macromolecular compounds according to the present invention have a superior surface activity.

The following Examples 1, 3 and 4 are given to illustrate, without limitation, the present invention. Example 2 is given for purposes of comparison:

EXAMPLE 1

Starting Materials molecular sieve material based on cross-linked dextran
glucose oxidase (220 U/mg.)
acrylamide
N,N'-methylene-bis-acrylamide
acryloyl chloride
ammonium peroxydisulfate
N,N-dimethylamino-propionitrile

Method 100 mg. glucose oxidase were dissolved in 5 ml. 0.5M triethanolamine buffer (pH 8.0) and cooled to 10° C. in an atmosphere of nitrogen. To this reaction batch were added 0.03 ml. acryloyl chloride in 2 ml. methylene chloride and the reaction mixture was then stirred for 30 minutes. In this enzyme solution preincubated with acryloyl chloride were dissolved 0.8 g. acrylamide and 0.05 g. N,N'-methylene-bis-acrylamide. The polymerization was then initiated with 0.05 ml. 5% N,N-dimethylaminopropionitrile solution, as well as 0.05 ml. 5% ammonium peroxydisulfate solution. Immediately after this addition, 5 g. of molecular sieve material (Sephadex G-25, medium) were added to the reaction batch and this was then stirred in an atmosphere of nitrogen.

The volume of the reaction solution was so calculated that it was not sufficient for the complete swelling of the molecular sieve so that a uniform polymerization block was not formed but rather the polymerization took place exclusively within the molecular sieve particles. The material obtained was suspended in 500 ml. distilled water, vigorously slurried with a stirrer, filtered off with suction and lyophilized. There were obtained about 5 g. (referred to the lyophilizate) of material with a specific activity of 160 U/g. lyophilizate.

EXAMPLE 2 (Comparison)

Starting Materials

Sephadex G-25, medium
glucose oxidase (220 U/mg.)
cyanogen bromide

Method 5 g. Sephadex G-25 were swollen with 75 ml. water and mixed with 100 ml. of a 2.5% cyanogen bromide solution. The pH value was immediately adjusted to 11 and kept constant at this value for 6 minutes by the addition of a 2N aqueous solution of sodium hydroxide. Subsequently, the material was washed with an aqueous 0.1M sodium bicarbonate solution. The cyanogen bromide-activated Sephadex was then mixed with 200 mg. glucose oxidase, dissolved in 10 ml. 0.5M triethanolamine buffer (pH 8.0). The reaction batch was left to stand for eighteen hours at 4° C. Subsequently, the material was washed with 0.2M phosphate buffer (pH 7.5). The specific activity of the carrier-bound enzyme thus obtained was 38 U/g.

The fixing reaction of proteins by the cyanogen bromide-activation of cross-linked polysaccharides has hitherto been regarded as being the method giving the highest activity yields. However, a comparison of Examples 1 and 2 shows that, in spite of the use of twice as much enzyme, referred to the carrier, according to the known process, there was obtained a product with an activity which is less than 25% of the activity achieved by means of the process according to the present invention. Referred to the amount of enzyme used, the activity yield was, in the case of the process of the present invention, eight times higher.

EXAMPLE 3

Starting Materials molecular sieve material based on cross-linked polyacrylamide
glucose oxidase (220 U/mg.)
acrylamide
N,N'-methylene-bis-acrylamide
acryloyl chloride
methylene chloride
ammonium peroxydisulfate
N-dimethylaminopropionitrile

Method

The preincubation of the enzyme solution took place in the manner described in Example 1.

Immediately after the addition of the initiator solutions, 5 g. molecular sieve (Biogel P6 50–100 mesh) were added to the reaction batch and this was then stirred in an atmosphere of nitrogen. The swelling of the molecular sieve first took place after a few seconds so that a good mixing up was achieved.

The volume of the reaction solution was so calculated that it was not sufficient for the complete swelling of the molecular sieve so that a uniform polymerization block was not formed but rather the polymerization took place exclusively within the molecular sieve particles. The material obtained was suspended in 500 ml. distilled water, vigorously slurried with a stirrer and subsequently fractionated through two standard sieves of 0.4 and 0.2 mm. mesh size. The particles with a size of 0.2–0.4 mm. were placed into a column of 20 mm. diameter and eluted with 4 liters of 0.2M phosphate buffer (pH 7.5). There were obtained about 5 g. of material (referred to the dry mass); specific activity 160 U/g. (referred to the dry mass).

EXAMPLE 4

Starting Materials polyadenylic acid (poly A)
triethanolamine buffer (0.5M, pH 8.0)
acryloyl chloride
ether
acrylamide
N,N'-methylene-bis-acrylamide
N,N-dimethylaminopropionitrile (5%)
ammonium peroxydisulfate (5%)
Sephadex G-25, medium Method 27.4 mg. poly A were dissolved in 2 ml. triethanolamine buffer and cooled to 10° C. To this reaction solution were added, in an atmosphere of nitrogen, 0.01 ml. acryloyl chloride, dissolved in 1 ml. ether, and the mixture was stirred for thirty minutes. Subsequently, the reaction mixture was mixed with 0.3 g. acrylamide and 0.2 g N,N'-methylene-bis-acrylamide, as well as with 2 g. Sephadex G-25, and the polymerization of the suspension was initiated with 0.02 ml. N,N-dimethylaminopropionitrile and 0.02 ml. ammonium peroxydisulphate. The granular product obtained was, after eight hours, placed into a column and washed with 2.5 liters 0.5M aqueous sodium chloride solution.

For the detection of the poly A bound on to the Sephadex by surface fixing, the product was suspended in 0.3N aqueous potassium hydroxide solution and hydrolyzed overnight at 37° C.

The nucleic acid concentration obtained after hydrolysis was about 10%, calculated upon the amount of poly A initially used.

It will be understood that the specification and examples are illustrative but not limitative of the present invention and that other embodiments within the spirit and scope of the invention will suggest themselves to those skilled in the art.

What is claimed is:

1. Process for the preparation of a carrier-bound macromolecular compound comprising reacting in solution a biologically active protein A with a coupling compound B which contains at least one reactive function capable of coupling with the biologically active protein A and at least one further reactive polymerizable group, adding to the resulting coupled reaction product AB in the form of a polymerizable solution having a polymerizable system therein a partially cross-linked molecular sieve material in essentially unswollen state, in an amount which cannot be completely swollen by said polymerizable solution of AB, the degree of cross-linking of the molecular sieve being such as to exclude the biologically active protein A, drawing said polymerizable solution into said molecular sieve material during swelling thereof so that said polymerizable solution and compound B are present substantially in the interior of the molecular sieve material and the biologically active protein is present substantially on the surface of said molecular sieve material, and polymerizing the polymerizable group of the coupled product AB in said polymerizable solution in the interior of the molecular sieve material whereby a polymer body is formed substantially within said molecular sieve material and said protein is fixed substantially on the surface of said molecular sieve material and is bound to said polymer therein.

2. Process as claimed in claim 1, wherein the biologically active protein A is an enzyme, an antibody or a hormone.

3. Process as claimed in claim 1, wherein a compound B is used which, as the couplable function, carries an alkylation or acylation group and, as the polymerizable function, carries a carbon-carbon or carbon-oxygen double bond.

4. Process as claimed in claim 3, wherein the couplable function in compound B is an oxirane, ethyleneimine, halide, acid halide, azide or anhydride group.

5. Process as claimed in claim 1, wherein the compound B used has the formula:

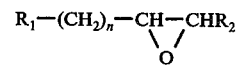

in which $R_1$ is a mono- or polyunsaturated aliphatic hydrocarbon radical, which optionally contains at least one oxo group adjacent to a double bond, and $R_2$ is hydrogen or lower alkyl.

6. Process as claimed in claim 1, wherein the compound B used is acryloyl chloride, allyl bromide, maleic anhydride, maleic acid azide, 1-allyloxy-3-(N-ethyleneimine)-propan-2-ol, acrylic acid 2,3-epoxypropyl ester, but-2,3-ene oxide, methacrylic acid 2,3-epoxypropyl ester, maleic acid 2,3-epoxypropyl monoester, fumaric acid epoxy-(2,3-epoxypropyl ester), fumaric acid epoxy-(2,3-epoxypropyl diester) or 1-allyloxy-2,3-epoxybutane.

7. Process as claimed in claim 1, wherein the molecular sieve material used is a cross-linked dextran or a cross-linked agar.

8. Process as claimed in claim 1, wherein the molecular sieve material used is a cross-linked polyacrylamide.

9. Process as claimed in claim 1, wherein the polymerization of the coupling product AB is carried out in the presence of a further copolymerizable and/or polymerization-promoting compound.

10. Process as claimed in claim 1, wherein the biologically active protein is an enzyme, the coupling compound B is selected from the group consisting of acryloyl chloride, allyl bromide, maleic anhydride, maleic acid azide, 1-allyloxy-3(N-ethyleneimine)-propan-2-ol, acrylic acid 2,3-epoxypropyl ester, but-2,3-ene oxide, methacrylic acid 2,3-epoxypropyl ester, maleic acid 2,3-epoxypropyl monoester, fumaric acid epoxy-(2,3-epoxypropyl ester), fumaric acid epoxy (2,3-epoxypropyl diester) and 1-allyloxy-2,3-epoxybutane and the molecular sieve is a cross-linked dextran, agar or polyacrylamide.

11. Carrier-bound biologically active protein prepared by the process claimed in claim 1.

12. Carrier-bound biologically active protein as claimed in claim 11 wherein the biologically active protein is an enzyme, the molecular sieve material is a cross-linked dextran, agar or polyacrylamide and the coupling compound B is selected from the group consisting of acryloyl chloride, allyl bromide, maleic anhydride, maleic acid azide, 1-allyloxy-3-(N-ethyleneimine)-propan-2-ol, acrylic acid 2,3-epoxypropyl ester, but-2,3-ene oxide, methacrylic acid 2,3-epoxypropyl ester, maleic acid 2,3-epoxypropyl monoester, fumaric acid epoxy-(2,3-epoxy-propyl ester), fumaric acid epoxy-(2,3-epoxy-propyl diester), and 1-allyloxy-2,3-epoxybutane.

* * * * *